(12) United States Patent
Rutynowski et al.

(10) Patent No.: US 6,613,064 B2
(45) Date of Patent: Sep. 2, 2003

(54) ARRANGEMENT REGULATING DEPTH OF THE PUNCTURE, USED IN THE DEVICE FOR PUNCTURING

(75) Inventors: Wlodzimierz Rutynowski, Warsaw (PL); Wojciech Wyszogrodzki, Warsaaw (PL)

(73) Assignee: P.Z. "HTL" S.A., Warsaw (PL)

( * ) Notice: Subject to any disclaimer, the term of this patent is extended or adjusted under 35 U.S.C. 154(b) by 44 days.

(21) Appl. No.: 09/814,094

(22) Filed: Mar. 22, 2001

(65) Prior Publication Data

US 2001/0039387 A1 Nov. 8, 2001

(30) Foreign Application Priority Data

Apr. 4, 2000 (PL) .......................................... P 339 530

(51) Int. Cl.[7] ................................................. A61F 17/34
(52) U.S. Cl. ....................................... 606/185; 606/182
(58) Field of Search ................................ 606/181, 182, 606/184, 185, 186, 187, 188, 189; 600/583, 573; 604/110, 134, 136, 157; 128/907

(56) References Cited

U.S. PATENT DOCUMENTS

| | | | | |
|---|---|---|---|---|
| 5,147,375 A | * | 9/1992 | Sullivan et al. | 606/182 |
| 5,356,420 A | | 10/1994 | Czernecki et al. | 606/182 |
| 5,569,287 A | * | 10/1996 | Tezuka et al. | 606/182 |
| 5,730,753 A | * | 3/1998 | Morita | 606/181 |
| 6,053,930 A | * | 4/2000 | Ruppert | 606/181 |
| 6,210,420 B1 | * | 4/2001 | Mauze et al. | 606/182 |
| 6,248,120 B1 | * | 6/2001 | Wyszogrodzki | 606/182 |

* cited by examiner

Primary Examiner—A. Vanatta
(74) Attorney, Agent, or Firm—Michael D. Bednarek; Shaw Pittman LLP

(57) ABSTRACT

An arrangement for regulating the depth of a puncture including a sleeve, a button placed at one end of the sleeve, a piston with a puncturing tip that is slidably mounted within the sleeve, and a power spring placed between the front of the button and the piston. The other end of the sleeve (1) includes an adjusting ring (3), which has two inwardly directed half-ringed, oblique limiting members (14, 15), which are hit by fin (7) of the piston during puncturing of skin.

4 Claims, 2 Drawing Sheets

ARRANGEMENT REGULATING DEPTH OF THE PUNCTURE, USED IN THE DEVICE FOR PUNCTURING

Present invention relates to arrangement regulating depth of puncture, used in the device for puncturing suitable for puncturing patient's skin in order to collect blood sample for the diagnostics purposes.

U.S. Pat. No. 5,356,420 discloses device for puncturing comprising sleeve and button placed at one end of the sleeve. The other end of the sleeve comprises a bottom with an opening. Within the sleeve there is a slidably mounted piston, piston is terminated with a pusher at the end pointed towards the button, and with puncturing tip and at the end pointed towards the bottom. Within the sleeve, the power spring is placed between the front of the button and the piston, the return spring is placed between the piston and the bottom of the sleeve. On the outer circumference of the piston, there are placed wings resisting on internal projection of the sleeve.

The essence of arrangement regulating the depth of the puncture, used in the device for puncturing according to the invention comprising sleeve, button placed at one end of the sleeve, piston with puncturing tip slidably within the sleeve and power spring between the front of the button and piston, is that, at the other end of the sleeve is mounted adjusting ring with the opening receiving the puncturing tip, which has two inwardly directed half-ringed, oblique or arranged in steps limiting members, in which during puncturing piston's skin, fin of the piston hits.

Preferably the side surface adjusting ring is provided with the marker, and on the outer surface of the sleeve there is place a scale indicating the depth of the puncture.

Solution according to the invention provides regulation of depth of the puncture made with the device for puncturing the patient's skin.

The subject matter of the invention will be understood more fully from the detailed description given below and from the accompanying drawing of various embodiments of the invention in which.

Figure 1:
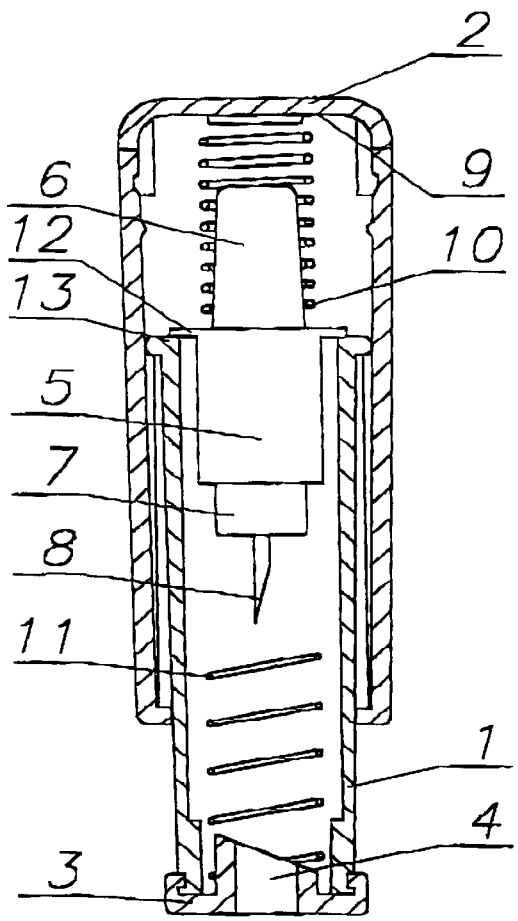
FIG. 1 shows longitudinal section of the device for puncturing with the arrangement for regulating the depth of the puncture before its use.

Device for puncturing showed in FIG. 1 comprises sleeve 1 and button 2, which is placed at one end of the sleeve 1 and houses said sleeve 1 at significant length. At the other end of the sleeve 1 is the adjustment ring 3 with opening 4. Within the sleeve 1 is slidably mounted piston 5 terminated from the side of the button 2, with the pusher 6 and from the side of adjustment ring 3, terminated with the fin 7 with puncturing tip 8. Inside the arrangement, between front 9 of the button 2 and piston 5, there is provided the power spring 10, within sleeve 1, between piston 5 and adjusting ring 3, there is provided the return spring 11. Piston 5 has in the upper part outwardly directed wings 12, which rest on the upper edge 13 of the sleeve 1.

Figure 2:
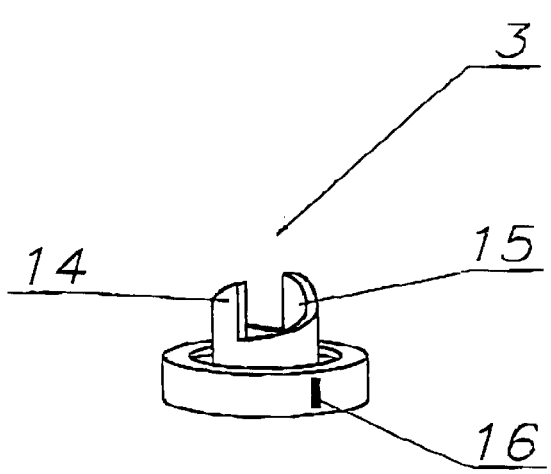
FIG. 2 shows the view of adjusting ring with two half-ringed, oblique limiting members.

In FIG. 2 is shown a view of adjusting ring 3. Adjusting ring 3 with the opening 4 receiving the puncturing tip 8, has directed inwardly into the sleeve 1, two half-ringed, oblique limiting members 14, 15, which allow smooth adjusting of the puncture's depth. It's obvious, that one may use limiting members arranged in steps instead oblique limiting members 14, 15, which allow regulation of the puncture's depth in stepped way. Moreover, as shown in FIG. 3 the side surface adjusting ring 3 is provided with marker 16, and the outer surface of the sleeve 1 is provided with scale 17 placed in front of marker 16, indicating depth of the puncture.

Device with arrangement for regulation of the puncture's depth according to the present invention works as follows. Position of the device's elements before its use is shown in FIG. 1. Wings 12 of the piston 5 rest on the upper edge 13 of the sleeve 1, in a result of action of the power spring 10. In this way piston 5 with puncturing tip 8 is hold in the first stable position. Pushing the button 2 causes compression of the power spring 10 until the moment in which, the front 9 of the button 2 rest on pusher 6 of the piston 5. Further pushing of the button 2 causes braking out of the wings 12 of the piston 5, and the power spring 10 driving the piston 5 causes the fin 7 of piston 5 to hit the members 14, 15 limiting the puncture's depth, while the puncturing tip 8 moving through the opening 4 of the adjusting ring 3 punctures the patient's skin. Next the return spring 11 pushes backward piston 5 with the puncturing tip 8, which then takes the second stable position inside the sleeve 1.

The depth of the puncture of the patient's skin is adjusted by turning the adjusting ring 3 in relation to the axis of the device, preferably with use of the ratchet mechanism. In this way one may change the position of the half-ringed, oblique limiting members 14, 15 in relation to fin 7 of the piston 5, and after fin 7 of the piston 5 hits limiting members, depth for which the puncturing tip 8 will penetrate the patient's body.

Figures 3, 4:
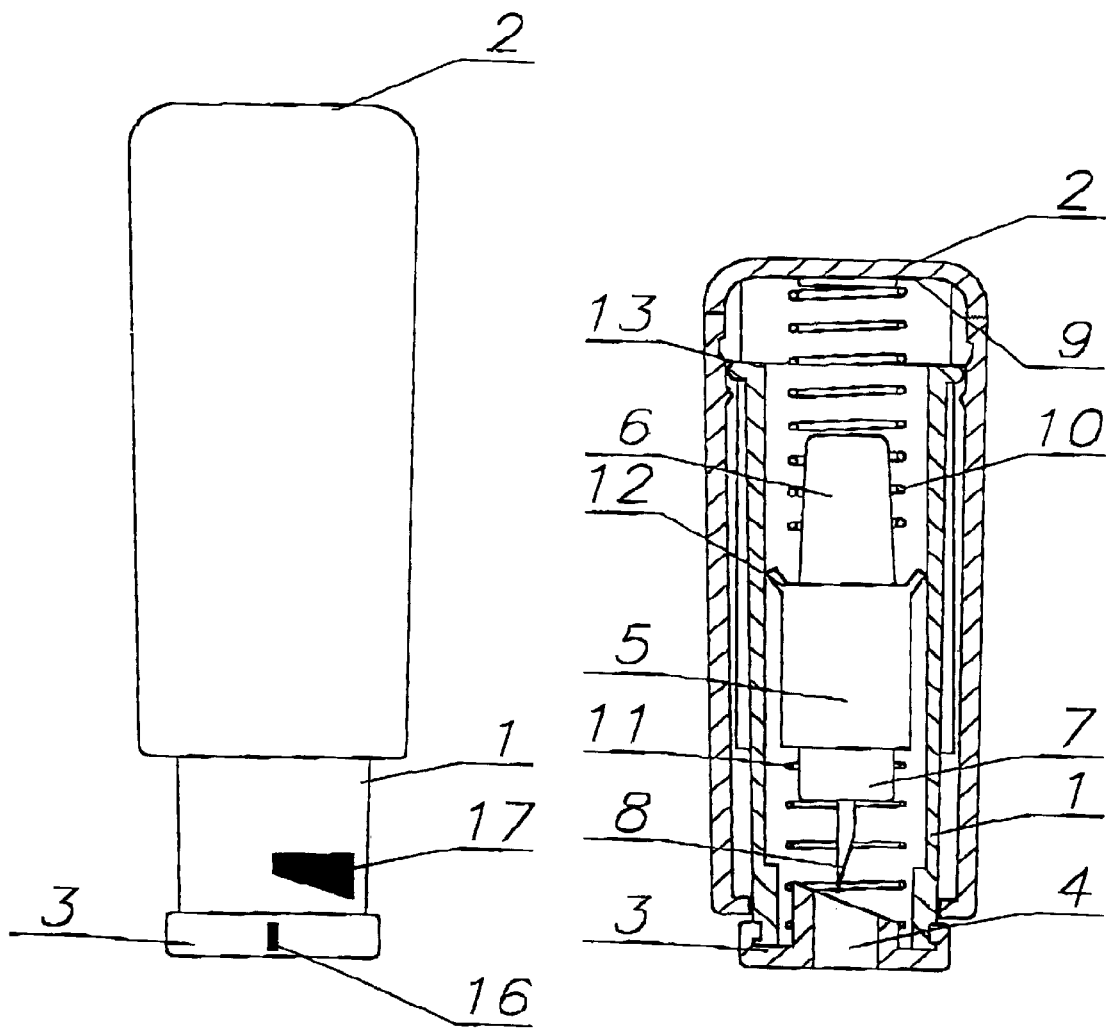
FIG. 3 shows side view of the arrangement with scale indicating depth of the puncture.
FIG. 4 shows longitudinal section of the device with the arrangement for regulating depth of the puncture, after its use.

Position of the elements of the device after its use is shown in FIG. 4, where the broken out wings 12 of the piston 5 are shown. Reuse of the device with wings 12 that are broken out is not possible.

What is claimed is:

1. A puncturing device for regulating depth of puncture comprising:
    a sleeve having a first end and a second end;
    a button disposed at the first end of the sleeve;
    a piston slidably mounted within the sleeve, wherein the piston has a puncturing tip and a fin;
    a spring between the button and the piston; and
    an adjusting ring mounted at the second end of the sleeve, wherein the adjusting ring has an opening for receiving the puncturing tip, wherein the adjusting ring has two inwardly directed half-ringed, oblique limiting members, and wherein the fin of the piston hits the limiting members during puncturing of a paient's skin.

2. The puncturing device of claim 1, wherein the adjusting ring has a side surface that is provided with a marker and wherein the sleeve has an outer surface that is provided with a scale indicating depth of puncture.

3. A puncturing device for regulating depth of puncture comprising:
    a sleeve having a first end and a second end;
    a button disposed at the first end of the sleeve;
    a piston slidably mounted within the sleeve, wherein the piston has a puncturing tip and a fin;
    a spring between the button and the piston; and
    an adjusting ring mounted at the second end of the sleeve, wherein the adjusting ring has an opening for receiving the puncturing tip, wherein the adjusting ring has two inwardly directed half stepped limiting members, and wherein the fin of the piston hits the limiting members during puncturing of a patient's skin.

4. The puncturing device of claim 3, wherein the adjusting ring has a side surface that is provided with a marker and wherein the sleeve has an outer surface that is provided with a scale indicating depth of puncture.

* * * * *